US007150984B2

(12) United States Patent
Hoshino et al.

(10) Patent No.: US 7,150,984 B2
(45) Date of Patent: Dec. 19, 2006

(54) ATTENUATED HUMAN ROTAVIRUS VACCINE

(75) Inventors: Yasutaka Hoshino, Wheaton, MD (US); Albert Z. Kapikian, Rockville, MD (US); Robert M. Chanock, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/500,564

(22) Filed: Jul. 11, 1995

(65) Prior Publication Data

US 2002/0058043 A1     May 16, 2002

Related U.S. Application Data

(63) Continuation-in-part of application No. 08/481,644, filed on Jun. 7, 1995, now abandoned, which is a continuation-in-part of application No. 08/273,056, filed on Jul. 11, 1994, now abandoned.

(51) Int. Cl.
*C12N 7/04*     (2006.01)
*C12N 7/08*     (2006.01)
*A61K 39/15*     (2006.01)

(52) U.S. Cl. .................... 435/236; 435/237; 424/215.1
(58) Field of Classification Search ............. 424/715.1
See application file for complete search history.

(56) References Cited

U.S. PATENT DOCUMENTS

| | | | | |
|---|---|---|---|---|
| 4,571,385 | A | * | 2/1986 | Greenberg et al. ........ 435/172.3 |
| 4,624,850 | A | * | 11/1986 | Albert et al. ................. 424/89 |
| 4,927,628 | A | * | 5/1990 | Chanock et al. .............. 424/89 |
| 5,147,639 | A | * | 9/1992 | Welter et al. ................. 424/89 |
| 5,298,244 | A | | 3/1994 | Redmond et al. |

OTHER PUBLICATIONS

Glass R, Gentsch J, Smith J; Rotavirus vaccines: Success by Reassortment; Science 265: 1389-1391, Sep. 1994.*
Kapikian A,Hoshino Y,Flores J,Midthun K, Glass R,Nakagomi O,Nakagomi T,Chanock R,Potash L,Levine M, Dolin R,Wright P,Belshe R,Anderson E,Vesikari T,Gothefors L,Wadell G,Perez-Schael I; Alternative approaches to the development of a rotavirus vaccine; 11th NoBel Conf., Stockholm: 192-214, 1985.*
Bernstein D, Smith V, Sander D, Pax K, Schiff G, Ward R; Evaluation of WC3 rotavirus vaccine and correlates of protection in healthy infants; J. Infect. Dis. 162:1055-1062, 1990.*
Matsuno S, Murakami S, Takagi M, Hayashi M, Inouye S, Hasegawa A, Fukai K; Cold-adaptation of human rotavirus; Virus Res. 7:273-280, 1987.*
Vesikara T, Ruuska T, Koivu H, Green K, Flores J, Kapikian A; Evaluation of the M37 human rotavirus vaccine in 2- to 6-month-old infants; Pediatr. Infect. Dis. J. 10(12):912-917, 1991.*
Lerner et al., in The biology of immunologic disease; eds. Dixon F and Fisher D; HP Publishing Inc:331-338, 1983.*
Greenberg et al., "Rescue of Noncultivatable Human Rotavirus by Gene Reassortment During Mixed Infection with ts Mutants of a Cultivatable Bovine Rotavirus," *Proc. Natl. Acad. Sc.* USA 78:420-424 (Jan. 1981).
Kalica et al., "Genes of Human Strain WA and Bovine Strain UK Rotaviruses that Code for Neutralizaiton and Subgroup Antigens," Biosys Abstract No. 82:149917 (1981).
Gombold et al., "Assignment of Simian Rotavirus SA11 Temperature-sensitive Mutant Groups B and E to Genome Segments," Medline Abstract No. 86045886 (May 1985).
Wyatt et al., "Human Rotavirus Type 2: Cultivation In Vitro," *Science* 207: 189-191 (1980).
Vesikari et al., "Immunogenicity and Safety of Live Oral Attenuated Bovine Rotavirus Vaccine Strain RIT 4237 in Adults and Young Children," *Lancet* 2:807-811 (1983).
Lerner et al., "The Development of Synthetic Vaccines", in *The Biology of Immunology Disease*, Dixon and Fisher, eds., HP Publishing Co., pp. 331-338 (1983).
Hoshino et al., "Independent Segregation of Two Antigenic Specificities (VP3 and VP7) involved in Neutralization of Rotavirus Infectivity," *Proc. Natl. Acad. Sci.* USA 82:8701-8704 (1985).
Kapikian et al., "Rhesus Rotavirus: A Candidate Vaccine for Prevention of Human Rotavirus Disease," *Vaccine 85*, Eds. Lerner et al., Cold Spring Harbor Laboratory, NY, pp. 357-367 (1985).
Midthun et al., "Reassortant Rotaviruses as Potential Live Rotavirus Vaccine Candidates," *J. Virol.* 53:949-954 (1985).
Shaw et al., "Specific Enzyme-Linked Immunoassay for Rotavirus Serotypes," *J. Clin. Microbiol.* 22:286-291 (1985).
Midthun et al., "Single Gene Substitution Rotavirus Reassortants Containing the Major Neutralization Protein (VP7) of Human Rotavirus Serotype 4," *J. Clin. Microbiol.* 24:822-826 (1986).
Clark et al., "Response of Adult Human Volunteers to Oral Administration of Bovine and Bovine/Human Reassortant Rotaviruses," *Vaccine* 4:25-31 (1986).
Offit et al., "Identification of the Two Rotavirus Genes Determining Neutralization Specificities," *J. Virol.* 57:376-378 (1986).
Clark et al., "Immune Response of Infants and Children to Low-Passage Bovine Rotavirus (Strain WC3)," *Am. J. Dis. Child.* 140:350-356 (1986).
Matsuno et al., "Cold-Adaption of Human Rotavirus," *Virus Res.* 7:273-280 (1987).

(Continued)

*Primary Examiner*—J. S. Parkin
(74) *Attorney, Agent, or Firm*—Townsend and Townsend and Crew LLP

(57) ABSTRACT

The present invention provides vaccine compositions of attenuated human rotavirus. More particularly, the attenuated human rotavirus is produced by cold passage and thus contains attenuating mutations which produce virus having a cold-adapted (ca) and temperature sensitive (ts) phenotype. The attenuated strains are used in methods for stimulating the immune system of an individual to induce protection against human rotavirus by administration of the ca attenuated rotavirus.

49 Claims, No Drawings

OTHER PUBLICATIONS

Taniguchi et al., "Direct Serotyping of Human Rotavirus in Stools by an Enzyme-Linked Immunosorbent Assay Using Serotype 1-, 2-, 3-, and 4-Specific Monoclonal Antibodies to VP7," *J. Infect. Dis.* 155:1159-1166 (1987).

Hoshino et al., "Infection Immunity of Piglets to Either VP3 of VP7 Capsid Protein Confers Resistance to Challenge with a Virulent Rotavirus Bearing the Corresponding Antigen," *J. Virol.* 62:744-748 (1988).

Kapikian et al., "Development of a Rotavirus Vaccine by a "Jennerian" and a Modified "Jennerian" Approach," *Vaccines 88*, p. 151-159 (1988).

Flores et al., "Reactions to and Antigenicity of Two Human-Rhesus Rotavirus Reassortant Vaccine Candidates of Serotypes 1 and 2 in Venezuelan Infants," *J. Clin. Microbiol.* 27:512-518 (1989).

Bernstein et al., "Evaluation of WC3Rotavirus Vaccine and Correlates of Protection in Healthy Infants," *J. Infect. Dis.* 162:1055-1062 (1990).

Green et al., "Homotypic and Heterotypic Epitope-Specific Antibody Responses in Adult and Infant Rotavirus Vaccinees: Implications for Vaccine Development," *J. Infect. Dis.* 161:667-679 (1990).

Flores et al., "Comparison of Reactogenicity and Antigenicity of M37 Rotavirus Vaccine and Rhesus-Rotavirus-Based Quadrivalent Vaccine," *Lancet* 2:330-334 (1990).

Padilla-Noriega et al., "Diversity of Rotavirus Serotypes in Mexican Infants with Gastroenteritis," *J. Clin. Microbiol.* 28:1114-1119 (1990).

Perez-Schael et al., "Clinical Studies of a Quadrivalent Rotavirus Vaccine in Venezuelan Infants,"*J. Clin. Microbiol.* 28:553-558 (1990).

Vesikari et al., "Evaluation of the M37 Human Rotavirus Vaccine in 2- to 6-Month-Old Infants," *Pediatr. Infect. Dis.* 10:912-917 (1991).

Kapikian et al., "An Update on the "Jennerian" and Modified "Jennerian" Approach to Vaccination of Infants and Young Children against Rotavirus Diarrhea," *Adv. Exp. Med. Biol.*, 327:59-69 (1992).

Vesikari, "Clinical Trials of Live Oral Rotavirus Vaccines: the Finish Experience," *Vaccines 93* 11:255-261 (1993).

Hoshino et al., "Genetic Determinants of Rotavirus Virulence Studied in Gnotobiotic Piglets," *Vaccines*, pp. 277-282 (1993).

Dennehy et al., "Safety and Efficacy of an Oral Tetravalent Rhesus Rotavirus Vaccine (RRV-TV) in Healthy Infants," Abst. No. 1052, *APS-SPR* (1994).

Glass et al., "Rotavirus Vaccines: Success by Reassortment?" *Science*, 265:1389-1391 (Sep. 2, 1994).

* cited by examiner

ATTENUATED HUMAN ROTAVIRUS VACCINE

RELATED APPLICATIONS

This application is a Continuation-in-Part of U.S. Ser. No. 08/481,644, filed Jun. 7, 1995, now abandoned, which is a Continuation-in-Part of U.S. Ser. No. 08/273,056, filed Jul. 11, 1994, now abandoned, each of which is incorporated in its entirety herein by reference.

BACKGROUND OF THE INVENTION

It is not generally appreciated that diarrheal diseases take an enormous toll in regard to morbidity and mortality in infants and young children in the developing countries of the world. Diarrheal diseases are ranked first among infectious diseases in the number of episodes and deaths in developing countries in Asia, Africa and Latin America. It is estimated that 5–10 million diarrhea-associated deaths occur annually in developing countries, predominantly in infants and young children. Walsh and Warren, *N. Engl. J. Med.* 301: 967 (1979).

Up until the 1970s, the cause of a major portion of diarrheal illnesses was not known. The rotavirus, discovered in 1973, has since been established as the single most important etiologic agent of severe diarrhea in infants and young children in the developed as well as developing countries, being responsible for approximately 35–50% of such illnesses. In the United States, 90% of infants and young children have experienced a rotavirus infection by the end of their third year of life. Kapikian and Chanock, in "Virology," 2d ed., Fields et al., eds., Raven Press, New York, pp. 1353–1404 (1990). The disease burden annually in the United States for rotavirus diarrhea in the under-5 year age group is estimated to reach over 1 million cases of severe diarrhea, with approximately 110,00 children hospitalized annually with presumptive rotavirus gastroenteritis, resulting in 583,000 hospital days, and 150 deaths. Matson and Estes, *J. Infect. Dis.* 162: 598 (1990). In developing countries, rotaviruses are believed to be responsible for the death of over 870,000 infants and young children annually. Institute of Medicine, in "New Vaccine Development. Establishing Priorities. Diseases of Importance in Developing Countries," Nat'l Academy Press, Washington, D.C. , II: 308–318 (1986).

Rotaviruses are classified as a genus in the family Reoviridae. Rotaviruses are about 70 nm in diameter and have a doubled layered icosahedral protein capsid that consists of an inner and outer layer. Within the inner capsid is the core that contains the 11 segments of the double-strand RNA genome. Rotaviruses are classified serologically into seven distinct serogroups, A–G, and within each group are further divided into serotypes. Only Group A, B and C rotaviruses have been found in humans, and Group A viruses have clearly been established as causing significant disease. Group B viruses have been associated with epidemics predominantly in adults in China, and Group C viruses have been only sporadically isolated from children with diarrhea, and the clinical significance remains unclear. Only one non-A rotavirus, a Group C porcine strain, has been successfully cultivated. Within Group A rotaviruses, ten serotypes associated with human infection have been identified, of which four (numbered 1, 2, 3 or 4) are regarded as epidemiologically important.

Group A rotaviruses possess two outer capsid proteins that function as independent neutralization antigens, namely, VP4 (encoded by genome segment 4) and VP7 (encoded by genome segment 7, 8 or 9 depending on the strain) (Hoshino et al., *Proc. Natl. Acad. Sci. USA* 82:8701–8704 (1985) and Offit et al., *J. Virol.* 57:376–378 (1986)). As a consequence a binomial nomenclature is now used to designate rotaviruses. This nomenclature includes designation of VP4 and VP7 rotaviruses. Although initially VP7 was thought to be the dominant neutralization antigen, recent studies have shown that VP4 is as effective as VP7 in inducing neutralizing antibodies following infection of experimental animals (Hoshino et al., *J. Virol.* 62:744–748 (1988) or susceptible infants or young children (Flores et al., *J. Clin. Microbiol.* 27:512–518 (1989)). Also, antibodies to VP4 or VP7 are independently associated with resistance of gnotobiotic piglets to experimental challenge with virulent rotavirus (Hoshino et al., *J. Virol.* 62:744–748 (1988)).

Strategies for the development of rotavirus vaccines have, to date, been based on a "Jennerian" approach, which takes advantage of the antigenic relatedness of human and animal rotaviruses and the diminished virulence of animal rotavirus strains for humans. Kapikian et al., in *Vaccines* 88, Chanock et al. (eds.), p. 151–159, Cold Spring Harbor Laboratory Press, Cold Spring Harbor, N.Y. (1987). Three candidate live oral rotavirus vaccines that have been evaluated in various parts of the world were developed using this approach, where an antigenically-related live virus derived from a nonhuman host is used as a vaccine for immunization against its human virus counterpart. These vaccines contained bovine rotavirus strain NCDV (RIT4237) (VP7 serotype 6) (Vesikari et al., *Lancet* 2:807–811 (1983)), bovine rotavirus strain WC3 (VP7 serotype 6) (Clark et al., *Am. J. Dis. Child.* 140:350–356 (1986)), or rhesus monkey rotavirus (RRV) strain MMU18006 (VP7 serotype 3) (Kapikian et al., *Vaccines* 85, Eds. Lerner et al., Cold Spring Harbor Laboratory, N.Y., pp. 357–367 (1985)). The protective efficacy of the monovalent bovine or simian rotavirus vaccines has proved to be variable. This can be attributed to the fact that the target population of two- to five-month-old infants characteristically developed a homotypic immune response following vaccination (Kapikian et al., *Adv. Exp. Med. Biol.*, 327:59–69 (1992), Bernstein et al., *J. Infect. Dis.* 162: 1055–1062 (1990), Green et al., *J. Infect. Dis.* 161:667–679 (1990), and Vesikari, *Vaccine* 11:255–261 (1993)). As a consequence, a modified "Jennerian" approach was developed for the formulation of a tetravalent vaccine. This involved replacing the VP7 gene of the animal (rhesus or bovine) rotavirus by the corresponding gene of each of the human rotaviruses of major clinical importance except in the case of rhesus rotavirus which did not require a serotype 3 VP7 substitution because this simian virus has a serotype 3 VP7. (Kapikian et al., *Adv. Exp. Med. Biol.*, 327:59–69 (1992), Midthun et al., *J. Virol.* 53:949–954 (1985), Midthun et al., *J. Clin. Microbiol.* 24:822–826 (1986), and Clark et al., *Vaccine* 4:25–31 (1986).)

A "non-Jennerian" approach to vaccination has also been considered. Recently, naturally-attenuated strain of human rotavirus, M37 [VP4:2;VP7:1], was evaluated as a vaccine candidate in two- to six-month-old infants. It induced an immune response that was primarily strain-specific (Flores et al., *Lancet* 2:330–334 (1990) and Vesikari et al., *Pediatr. Infect. Dis.* 10:912–917 (1991)). However, it failed to induce significant protection against rotavirus diarrhea. Matsuno et al., *Virus Res.* 7:273–280 (1987)) have reported the selection of a ca human rotavirus strain IGV-80-3 (VP7 serotype 1) which grew efficiently at 25° C., but further characterization of the strain has not been provided.

VP7 is the only relevant rotavirus protective antigen present in candidate vaccines that are currently being evaluated for protective efficacy in humans. This is because these vaccines contain the VP4 of an animal rotavirus or a naturally-attenuated human rotavirus that is not related antigenically to the VP4 of any of the clinically important human rotaviruses.

Although the quadrivalent rhesus rotavirus vaccine provides resistance to serious rotavirus diarrheal disease in 80% of instances (Dennehy et al., Abst. No. 1052, *APS-SPR* (1994)) there is an urgent need for a more potent vaccine that provides close to complete protection against serious rotavirus diarrhea. In order to achieve this goal it will be necessary to incorporate both protective antigens (i.e., VP4 and VP7) of clinically important rotavirus serotypes into the vaccine. The level of attenuation of the live virus should be sufficiently balanced such that it is capable of propagating to levels adequate for inducing a protective immune response while restricting replication to a level that the virus does not cause clinical disease in the immunized individuals. Quite surprisingly, the present invention fulfills this and other related needs.

SUMMARY OF THE INVENTION

The present invention provides vaccine compositions of attenuated human rotavirus. The attenuated rotavirus is provided in an amount sufficient to induce an immune response in a human host, optionally in conjunction with a physiologically acceptable carrier and an adjuvant to enhance the immune response of the host. In certain embodiments the attenuated rotavirus is a derivative of rotavirus which has been incompletely attenuated by introduction of mutations which produce virus having a temperature sensitive (ts), cold-adapted (ca) or other growth restricting or attenuating mutation. The attenuated virus of the invention belongs to serogroup A or other serogroups, and virus from the serogroup(s) and/or multiple serotypes within any of these serogroup(s) may be combined in vaccine formulations for more comprehensive coverage against prevalent rotavirus infections. A preferred embodiment is attenuated virus of serogroup A having the serotype VP4 1A, VP7 1, such as cold adapted (e.g., 30° C.) strain D or WA. The vaccine will typically be formulated in a dose from about $10^3$ to about $10^6$ plaque-forming units (PFU) or more for maximal efficacy.

In other embodiments the invention provides methods for stimulating the immune system of an individual to induce protection against human rotavirus. These methods comprise administering to the individual an immunologically sufficient amount of human rotavirus which has been attenuated by introducing mutations that specify the ca phenotype and typically the ts phenotype. In view of the potentially serious consequences of rotavirus infection in infants and young children, and the elderly, these individuals will typically benefit most from immunization according to the present methods. In most instances the attenuated rotavirus is administered to the alimentary tract of the individual, preferably by liquid suspension or other solution.

In yet other embodiments the invention provides pure cultures of attenuated human rotavirus, wherein the virus has been attenuated by the introduction of two or more ca and ts mutations. The attenuated virus is capable of eliciting a protective immune response in an infected human host yet is sufficiently attenuated so as to not cause unacceptable symptoms of severe gastrointestinal disease in the immunized host. The attenuated human rotavirus may be present in a cell culture supernatant, recovered from the culture, or partially or completely purified. The virus may also be lyophilized, and can be combined with a variety of other components for storage or delivery to a host, as desired.

DESCRIPTION OF THE SPECIFIC EMBODIMENTS

The present invention provides attenuated rotavirus suitable for vaccine use in humans. The rotavirus described herein is produced by introducing mutations in wild-type or incompletely attenuated strains of human rotaviruses. The mutations are introduced in the strains during virus growth in cell cultures by selection of virus that has acquired the ability to grow efficiently at suboptimal temperature in order to introduce growth mutations.

Thus, the vaccine of the invention comprises the attenuated rotavirus and a physiologically acceptable carrier. The vaccine is administered in an immunogenically sufficient amount to an individual in need of immunological protection against rotavirus, such as, e.g., an infant, child or adult. The vaccine elicits the production of an immune response that is protective against serious rotavirus disease, such as severe diarrhea, when the individual is subsequently exposed to or infected with a wild-type human rotavirus. As the attenuated virus of the vaccine infects the host alimentary tract, some mild disease may occur as a result of the vaccination and possibly following subsequent infection by wild-type virus, but typically the vaccine will not cause clinically relevant disease in the vaccine when the virus is sufficiently attenuated and administered in an amount below that which causes such symptoms. Following vaccination, however, there are detectable levels of host engendered serum and secretory antibodies which are capable of neutralizing homologous (of the same serotypes) wild-type virus in vitro and in vivo. To achieve protection against serotypes which are prevalent epidemiologically, i.e., against serotypes VP7 1, VP7 2, VP7 3, and VP7 4, a cocktail of strains containing the different serotypes can be employed in the vaccine composition, up to and including a quadrivalent vaccine comprising each of the VP7 1–4 serotypes. Additional strains may be added (or omitted) as necessary to provide adequate immunological coverage for the strain prevalent in a particular geographic area.

The attenuated virus which is a component of the vaccine is in an isolated and typically purified form. By isolated is meant to refer to attenuated modified rotavirus which is in other than the native environment of wild-type virus, such as the gastrointestinal tract of an infected individual. More generally, isolated is meant to include the attenuated virus as a heterologous component of a cell culture or other system. For example, attenuated rotavirus of the invention may be produced by an infected cell culture, separated from the cell culture and added to a stabilizer, and may contain other non-naturally occurring rotaviruses to form a multivalent vaccine as described above.

The attenuated human rotavirus of the present invention exhibits a substantial diminution of virulence when compared to wild-type virus that is circulating naturally in infected humans. The attenuated human rotavirus is not so attenuated however, that all symptoms of infection will necessarily be absent in all immunized individuals. The attenuated virus is capable of replication, particularly in the gastrointestinal tract of the host. In some instances the attenuated virus may still be capable of dissemination to unvaccinated individuals. However, its virulence is sufficiently abrogated such that severe lower gastrointestinal tract infections or disease in the vaccinated or incidental host do not occur.

The level of attenuation may be determined by, for example, quantifying the amount of virus found in the gastrointestinal tract of an immunized host and comparing the amount to that produced by wild-type rotavirus or other attenuated rotaviruses which have been evaluated as candidate vaccine strains, such as those of rhesus monkey or bovine rotavirus strains. For example, the attenuated virus of the invention will have a greater degree of restriction of replication in the gastrointestinal tract of an infected host, such as an infant, child or adult, compared to the levels of replication of wild-type virus, e.g., 100- to 1000-fold less. The attenuated viruses of the invention must be sufficiently infectious and immunogenic in humans to confer effective protection in vaccinated individuals. Methods for determining levels of rotavirus in the gastrointestinal tract of an immunized host are well known in the literature and are described in the Example section below. For example, specimens obtained by stool sample or swab are suspended in buffer and virus quantified in tissue culture or other by laboratory procedure. See, for example, Kapikian et al., in Lennette and Schmidt (ed.), *Diagnostic Procedures for Viral. Rickettsial. and Chlamydial Infections,* 5th ed., p. 927–995, Amer. Public Health Assoc., Washington, D.C. (1979), which is incorporated herein by reference.

To produce a satisfactorily attenuated human rotavirus of the present invention mutations are introduced into a parental wild-type viral strain which has been isolated from a clinical sample or other source. For rotavirus of serogroup A, the parental wild-type virus is preferably serotypes VP4 1A or 1B. With regard to VP7 serotype, the parental wild-type virus is preferably serotype VP7 1, VP7 2, VP7 3 or VP7 4, although other parental serotypes may be employed as necessary.

Attenuated human rotavirus mutants can also be produced by biologically cloning wild-type virus in an acceptable cell substrate and developing cold-adapted mutants thereof, and by subjecting the virus to mutagenic pressures, e.g., chemical mutagenesis or even neutralizing monoclonal antibodies, to produce ts mutants or other attenuating mutants. The various selection techniques may also be combined to produce the attenuated mutants of human rotavirus which are useful as described herein.

According to the present invention the ca mutants are produced by subjecting the parental wild-type or even a partially attenuated virus strain to passage in cell culture at progressively lower, suboptimal temperatures. For example, whereas wild-type virus is typically cultivated at about 37–39° C., the partially attenuated mutants are produced by repeated passage in cell cultures (e.g., African green monkey kidney cells, AGMK) at suboptimal temperatures, e.g., from about 30° C. down to about 26° C. These mutants demonstrate evidence of cold adaptation (ca) by increased efficiency of growth at the lower temperature compared to the wild-type (or partially attenuated) parental virus, and, in the process of becoming cold-adapted, typically demonstrate ts mutations, with shutoff temperature or plaque formation in cell cultures ranging from near 36° C. or 37° C., up to about 38° C. or even 39° C. Thus, in one method of the present invention the ca attenuated mutant human rotavirus strains are adapted to efficient growth at a lower temperature by passage in AGMK cells, down to a temperature of about 24–26° C., preferably 26–30° C. This selection of rotavirus mutant during cold-passage substantially eliminates significant virulence in the strains as compared to the virulent wild-type or partially attenuated parent strain. The level of temperature sensitivity of viral replication of the attenuated rotavirus of the invention is determined by comparing its replication at a permissive temperature with that at several restrictive temperatures. The lowest temperature at which the replication of the virus is reduced 100-fold or more in comparison with its replication at the permissive temperature is termed the shutoff temperature. Typically the replication and virulence of rotavirus correlate with the shutoff temperature. Replication of mutants with a shutoff temperature of 39° C. is moderately restricted, whereas mutants with a shutoff of 36–38° C. replicate even less well.

In addition to the criteria of attenuation and immunogenicity, the properties of the attenuated human rotaviruses which are selected must also be as stable as possible so that the desired attributes are maintained. While some genetic instability may be tolerated, virus useful in the vaccines of the present invention must retain the properties of attenuation, restriction of replication in the immunized host, and the ability to effectively elicit the production of an immune response in the vaccinee that is sufficient to confer protection against serious disease caused by subsequent infection by wild-type virus. It may be desirable to use two or more additional mutations or selection criteria, e.g., ca and ts, in one viral strain to more effectively attenuate the virus while retaining the ability to stimulate a protective immune response and in some instances to expand the protection afforded by multiple modifications, e.g., induce protection against different viral strains or subgroups, or protection of a different immunologic basis, e.g., secretory versus serum immunoglobulins, cellular immunity, and the like.

The attenuated virus of the invention may be propagated in a number of cell lines which permit rotavirus growth. Preferred cell lines for propagation of attenuated human rotavirus for vaccine use include AGMK and Vero cells. Cells are typically inoculated with virus at a multiplicity of infection ranging from about 0.1 to 1.0 or more, and are cultivated under conditions permissive to replication of the virus, e.g., at about 28°–35° C. and for about 3–5 days, or as long as necessary for virus to reach an adequate titer. Virus is removed from cell culture and separated from cellular components, typically by well known clarification procedures, e.g., centrifugation, and may be further purified as desired using procedures well known to those in the art.

Human rotavirus which has been attenuated as described herein can be tested in in vitro and in vivo models to confirm adequate attenuation and immunogenicity for vaccine use. In in vitro assays the modified virus is tested for the ability to (i) replicate at a suboptimal temperature when compared to the parental strain, and (ii) exhibit temperature sensitivity of plaque formation when compared to the parental strain. Mutant human rotaviruses are further tested in animal models of rotavirus infection. Animal models such as the gnotobiotic piglet are described in the Example section hereinbelow.

For vaccine use, the attenuated virus of the invention can be used directly in vaccine formulations, or lyophilized, as desired, using lyophilization protocols well known to the artisan, and then hydrated immediately prior to use. Lyophilized virus will typically be maintained at about 4° C. When ready for use the lyophilized virus is reconstituted in a stabilizing solution, e.g., citrate buffer, saline or the like, with or without adjuvant, as further described below.

Thus, rotavirus vaccines of the invention contain as an active ingredient an immunogenically effective amount of an attenuated cold adapted human rotavirus as described herein. The attenuated virus may be introduced into a host, particularly humans, with a physiologically acceptable carrier and/or adjuvant. Useful carriers are well known in the art, and include, e.g., citrate-bicarbonate buffer, buffered water, 0.4% saline, and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

Upon immunization with a attenuated rotavirus composition as described herein, via oral or parenteral route, the immune system of the host responds to the vaccine by producing antibodies, both secretory and serum, specific for rotavirus proteins. As a result of the vaccination the host becomes at least partially or completely immune to rotavirus infection, or if infection occurs the host is resistant to developing moderate or severe rotaviral disease, particularly of the lower gastrointestinal tract.

The vaccine compositions containing the attenuated human rotavirus of the invention are administered to a person susceptible to or otherwise at risk of rotavirus disease to enhance the individual's own immune response capabilities. Such an amount is defined to be a "immunogenically effective dose." In this use, the precise amounts again depend on the patient's age, state of health and weight, the mode of administration, the nature of the formulation, etc., but generally range from about $10^3$ to about $10^6$ plaque forming units (PFU) or more of virus per patient, more commonly from about $10^4$ to $10^5$ PFU virus per patient. In any event, the vaccine formulations should provide a quantity of attenuated rotavirus of the invention sufficient to effectively protect the patient against serious or life-threatening rotavirus infection.

The attenuated rotavirus of the invention of one particular rotavirus serotype can be combined with attenuated viruses of the other serotypes to achieve protection against multiple serotypes of human rotaviruses. Typically the different modified viruses will be in admixture and thus administered simultaneously, but in some instances they may be administered separately.

In some instances it may be desirable to combine the attenuated rotavirus vaccines of the invention with vaccines which induce protective responses to other agents, particularly other gastrointestinal viruses. For example, the attenuated virus vaccine of the present invention can be administered simultaneously (but typically separately) or sequentially with a Norwalk virus vaccine.

Single or multiple administrations of the vaccine compositions of the invention can be carried out. In neonates and infants, multiple administration may be required to elicit sufficient levels of immunity. Administration should begin within the first 2–4 months of life, and continue at intervals such as at one to two months or more after the initial immunization, as necessary to induce and maintain sufficient levels of protection against native (wild-type) rotavirus infection. Similarly, adults who are particularly susceptible to repeated or serious rotavirus infection, such as, for example, health care workers, day care workers, family members of young children, the elderly, etc. may require multiple immunizations to establish and/or maintain protective immune responses. Levels of induced immunity can be monitored by measuring amounts of neutralizing antibodies in serum and secretions, and dosages adjusted or vaccinations repeated as necessary to maintain desired levels of protection.

The following examples are offered by way of illustration, not by way of limitation.

EXAMPLE I

Production of Cold-Adapted Rotavirus Mutants

This Example describes human rotavirus mutants which were cold-adapted (ca) and temperature sensitive (ts), the mutants being produced and selected through extensive propagation at progressively lower temperatures.

Four strains of rotavirus, designated D (ATCC VR-970), Wa (ATCC VR-2018 and U.S. Pat. No. 4,341,870, incorporated herein by reference), DS-1 and P (U.S. Pat. No. 4,927,628, incorporated herein by reference), were originally obtained from children with diarrhea and were adapted directly to growth in primary African green monkey kidney (AGMK) cells (Whittaker Bioproducts, Walkersville, Md.). The relevant protective antigens of these viruses are: D, VP4 1A and VP7 1; Wa, VP4 1A and VP7 1; DS-1, VP4 1B and VP7 2; and P, VP4 1A and VP7 3.

To generate human×human rotavirus reassortants, primary tube cultures of AGMK cells were coinfected at a multiplicity of infection of approximately one with Wa and DS-1 viruses, or Wa and P viruses. When 50% to 75% of the cells exhibited cytopathic effects, the cultures were frozen and thawed once and the lysate was plated on primary AGMK cells in a six-well plate in the presence of serotype 1-specific VP7 neutralization monoclonal antibody 2C9. The desired reassortants were selected and plaque purified. Two reassortants, Wa×DS-1 and Wa×P, represented plaque progeny from the dual infection of AGMK cells with Wa and DS-1 or Wa and P. These reassortants derived ten genes from the Wa strain and only the VP7 gene from the DS-1 or P strain. This was determined from electrophoretic migration patterns of genomic RNAs of human rotavirus strains DS-1, Wa×DS-1 reassortant, strain Wa, Wa×P reassortant, and strain P. Genomic RNAs were electrophoresed at 13 mA for 16.5 hours, and the resulting migration patterns stained by silver nitrate.

The human rotavirus suspensions used to initiate cold passages to generate cold adapted mutants were prepared in AGMK cell cultures incubated at 37° C. The titer of these suspensions varied from $10^{5.0}$ to $10^{6.8}$ pfu/ml in assays performed at 37° C. Primary cultures of AGMK cells were used for passage of virus at the reduced temperatures during cold-adaptation, and for plaque purification and virus amplification.

Passage of viruses at the normal optimal (37° C.) or suboptimal (<37° C.) temperature was performed in conventional roller tube cell cultures. Incubation at suboptimal temperature was carried out by submerging the infected culture tubes in a water bath maintained at the appropriate temperature. The water baths were kept in a cold room (4° C.) to increase the temperature differential between the water bath and the environment. This allowed the temperature to be maintained within ±0.1° C. At the end of two weeks the infected cultures were frozen and thawed once and the lysate was passaged onto fresh primary AGMK cell cultures.

Rotaviruses D, DS-1, Wa×DS-1, and Wa×P were passaged initially at 37° C. Each of the viruses was restricted in ability to produce plaques at 30° C., as shown in Table 1, and for this reason 30° C. was chosen as the temperature for selection of ca mutants. The incubation temperature for strains D, DS-1, WaxP was then reduced to 30° C. Reassortant WaxDS-1 was passaged three times at 32° C. prior to passage at 30° C. Virus that produced plaques at 30° C. was not detected during the first two serial passages of D, DS-1, or WaxDS-1 at 30° C. The first evidence for selection of a ca mutant of D, DS-1, or WaxDS-1 was observed during the third serial passage at 30° C. A low titer of virus that produced plaques at 30° C. was detected in each instance. After an additional passage (D) or two additional passages (DS-1 and WaxDS-1) the titer of virus producing plaques at 30° C. increased, suggesting that one or more new mutations had been selected. A further increase in 30° C. plaque-forming virus occurred at the eighth (DS-1 or WaxDS-1) or ninth (D) cold passage, suggesting that at least one additional mutation had been selected. The first three serial passages of WaxP yielded a low titer of virus that produced plaques at 30° C.; the amount of such virus recovered after three cold passages did not differ significantly from that present in the inoculum used to initiate the passage series. Evidence for selection of one or more ca mutations in the WaxP virus was not observed until the fourth cold passage. A subsequent increase in titer of 30° C. plaque-forming virus was seen at the eighth passage.

Following the last serial passage of each strain at 30° C., a representative virus clone was isolated by three successive plaque-to-plaque passages at that temperature. In each instance, the virus that was cloned biologically after serial passage at 30° C. was a mutant that exhibited both the ca and ts phenotypes (Table 2).

The uncloned tenth passage harvest of the 30° C. series was then passaged serially ten times at 28° C. As before, virus triply plaque purified at 28° C. from the last passage of each 28° C. series was analyzed for its efficiency of plaque formation (eop) at various temperatures. In each instance, serial passage at 28° C. exerted selection for mutants that were both ca and ts. Subsequently, the uncloned harvest of the last passage at 28° C. was used to initiate ten serial passages at 26° C. In each instance, virus triply plaque purified at 26° C. from the last passage of the series retained the ca and ts phenotypes.

As noted above, after each low temperature passage series was completed, the 10th passage culture lysate was triply plaque purified in primary AGMK cells at the temperature of that passage series. Plaque-purified viruses were designated ca30-, ca28-, or ca 26-adapted virus. These plaque-purified viruses were not used to initiate the subsequent lower temperature passage but were used instead for characterization as representative clones of the passage series from which they were derived.

The established monkey kidney MA104 cell line was used for virus titration and plaque reduction neutralization (PRN) assays. Eagle's minimum essential medium supplemented with 0.5 µg/ml trypsin (SIGMA Type IX, St. Louis, Mo.) and antibiotics was used as maintenance medium. Hyperimmune antiserum to rotavirus Wa, DS-1, WaxDS-1, or WaxP was raised in specific-pathogen-free guinea pigs (National Cancer Institute, Bethesda, Md.) which were free of rotavirus neutralizing antibody (titer<1:20) as determined by PRN assay.

EXAMPLE II

Characterization of Cold-adapted Rotaviruses

Each plaque-purified ca rotavirus as well as its corresponding parental rotavirus strain were examined for plaque-forming efficiency at 26° C., 28° C., 30° C., 36° C., 37° C., 38° C., or 39° C. Six well plates containing monkey kidney MA104 cell monolayers were inoculated with decimal dilutions of virus suspension and incubated for one hour at 30° C., after which the wells were washed once with L-15 medium (Lebovitz) and the plates were then refed with overlay medium consisting of 0.6% agarose (SeaKem ME, FMC), Eagle's MEM, trypsin (0.5 µg/ml), and antibiotics. The plates were then incubated at 26° C., 28° C., 30° C. , 36° C., 37° C., 38° C., or 39° C. Cultures were incubated for eight days at 26° C. or 28° C., six days at 30° C., or five days at 36° C., 37° C., 38° C., or 39° C.

The clonal mutants selected at 30° C. were cold-adapted because plaque formation occurred with high efficiency at 30° C., a temperature at which wild-type parental virus did not form plaques efficiently (Table 2). However, each of these mutants was restricted in plaque formation at 28° C., i.e., plaque titer at 28° C. was 50-fold or more reduced compared to titer at 30° C. Each of the mutants was also temperature sensitive because plaque formation did not occur or was significantly reduced at 38° C. in the case of strain D or WaxP, or at 39° C. in the case of strain DS-1 or WaxDS-1 (Table 2). In contrast, wild-type parental virus produced plaques with high efficiency at 39° C.

In each instance, subsequent passage at 28° C. selected for a mutant that was more cold-adapted than the corresponding 30° C.-derived mutant which produced plaques efficiently at 30° C. but not at lower temperatures. In contrast, the clonal 28° C.-derived mutants produced plaques efficiently at 26° C. (D and DS-1) or 28° C. (WaxDS-1 or WaxP ). Three of the 28° C.-derived mutants also exhibited an increase in temperature sensitivity (D, DS-1, or WaxDS-1) as compared to the corresponding 30° C.-derived mutant.

Finally, three of the clonal mutants derived at 26° C. (DS-1, WaxDS-1, and WaxP ) were more cold-adapted than the corresponding 28° C. mutants. In the case of the 26° C. WaxP mutant, a greater degree of temperature sensitivity was noted compared to its corresponding 28° C. mutant.

Each plaque-purified ca rotavirus and corresponding parental rotavirus strain was also examined for maintenance of serotype by ELISA using type-specific anti-VP7 monoclonal antibodies. The monoclonal antibodies used in the ELISA analysis included the following: KU-4 (Taniguchi et al., *J. Infect. Dis.* 155:1159–1166 (1987)); 2C9 (Shaw et al., *J. Clin. Microbiol.* 22:286–291 (1985)), and 5E8 (Padilla-Noriega et al., *J. Clin. Microbiol.* 28:1114–1119 (1990)) (serotype 1-specific); S2-2G10 (Taniguchi et al., *J. Infect. Dis.* 55:1159–1166 (1987)) (serotype 2-specific); 954/159/13 (Greenberg et al., *J. Virol.* 47:267–275 (1983)), and YO-1E2 (Taniguchi et al., *J. Infect. Dis.* 55:1159–1166 (1987)) (serotype 3-specific); and ST-2G7 (Taniguchi et al., *J. Infect. Dis.* 55:1159–1166 (1987)) (serotype 4-specific). When tested by ELISA, the various ca, ts mutants of D, DS-1, WaxDS-1, or WaxP exhibited the same serotype-specific VP7 reactivity with VP7 monoclonal antibodies as the parental rotaviruses from which they were derived.

In addition, the identity of the mutants recovered after selection at the suboptimal temperature of 30° C., 28° C., or 26° C. was confirmed by gel electrophoresis of viral RNAs. The genotype (i.e., electropherotype) of each mutant appeared to be indistinguishable from that of its wild-type, parental virus. On the other hand, the genotype of each of the parental viruses was distinctive and easily differentiated from that of the other parental viruses.

Thus, in each instance, serial passage of four different human rotaviruses at the suboptimal temperature of 30° C. selected for a mutant that was able to produce plaques efficiently at 30° C. In contrast, parental virus did not produce plaques at 30° C. Each of the mutants also exhibited the ts phenotype. Mutants selected during the ten serial passages at 30° C. exhibited two or three discrete incremental increases in ability to replicate and produce plaques at this suboptimal temperature. Succeeding serial passage at the lower temperature of 28° C. selected for mutants that exhibited a greater degree of cold-adaptation. The 30° C.-derived mutants produced plaques efficiently at 30° C. but not at 28° C., whereas the 28° C.-derived mutants produced plaques efficiently at 28° C. or in several instances at 26° C. Three of the four 28° C.-derived ca, ts mutants exhibited a concomitant increase in temperature sensitivity. Finally, in three instances the next successive serial passage series, which was performed at the lower temperature of 26° C., selected for a mutant that exhibited an even greater degree of cold adaptation, associated in one instance with increased temperature sensitivity. These observations indicate that each of the viruses sustained a minimum of four to five mutations during the total selection procedure. Thus, the acquisition of this number of mutations should enhance the genetic stability of the recovered mutants.

During the course of the three-phase low temperature selection procedure, 12 mutants were recovered. Collectively, the mutants exhibited a relatively wide spectrum of growth restriction (as measured by efficiency of plaque formation) within the temperature range of 36° C. to 39° C. This degree of diversity enables selection of live rotavirus vaccine strains that exhibit the desired level of attenuation, immunogenicity, and protective efficacy.

An additional human rotavirus strain was subjected to sequential passage at the suboptimal temperatures of 30° C., 28° C. and 26° C. by methods identical to those described above. The parental virus was a reassortant derived from coinfection of AGMK cells with human rotavirus strain Wa (VP4:1A, VP7:1) and human rotavirus strain ST3 (VP4:2, VP7:4). The reassortant exhibited VP4:1A and VP7:4 serotype specificities. ca, ts mutants similar to those described above were recovered after passage in AGMK at 30° C., 28° C. and 26° C.

EXAMPLE III

Presence of the Attenuation Phenotype in Animals

The attenuation and immunogenicity of the ca rotavirus strains is determined in animal models and human clinical trials. Animal trials in gnotobiotic piglets are conducted according to the general protocol of Hoshino et al., *J. Virol.* 62:744–748 (1988), which is incorporated herein by reference. Four to five day old colostrum-deprived gnotobiotic piglets, derived by hysterectomy are housed in germ-free isolators and maintained generally as described in Bohl et al., *J. Clin. Microbiol.* 15:312–319 (1982). Individual piglets are given approximately $10^6$ PFU of the attenuated ca mutant virus by the alimentary route. The dose is chosen to be sufficient to assure the gnotobiotic piglets receive a fully infectious dose. Control piglets receive parental human rotavirus and a separate group receives no virus. The piglets are monitored daily for signs of illness. Rectal swabs are collected daily and virus replication and shedding is determined by cell culture immunofluorescence (CCIF) assay and/or by virus isolation and titration in cell culture (MA104 cells). Blood samples are collected prior to infection and three weeks later. All piglets, including the controls, are challenged orally 3 weeks after immunization with 2 ml of a parental wild-type (virulent) strain. Piglets are again examined daily for evidence of diarrhea, and rectal swabs are collected daily for 2 weeks postchallenge. Virus replication and shedding is determined by CCIF and/or by titration in MA104 cells. Blood samples are obtained two weeks after challenge.

As the Wa strain of human rotavirus causes mild to moderate diarrhea in gnotobiotic piglets some of the time (Wyatt et al., *Science* 207: 189–191 (1980), and Wa is identical to the D strain that was cold-adapted as described herein, virulence of various ca mutants of D strain may be assessed in piglets. Attenuation can be assessed by measuring the level of virus replication of parental D and its ca mutants in piglets. As the wild-type Wa strain grows to high titer in the intestines of piglets, comparison of the titer of virus in the intestines of piglets infected with parental (i.e., wild-type) D or mutant D yields information concerning attenuation of the mutants. Virus mutants that are restricted in their growth in vivo are most often attenuated for the host in which they exhibit restriction.

Ca mutant rotavirus which is sufficiently attenuated in gnotobiotic piglets grows in the intestines of the animals at a level approximately 500- to 1000-fold lower than wild-type parental virus. Moreover, virus obtained from the infected animals retains the laboratory markers of attenuation, i.e., cold adaptation and temperature sensitivity. The onset and duration of virus shedding are significantly reduced in piglets infected with the ca mutant. Piglets inoculated with an attenuated virus vaccine strain of the invention also demonstrate a significant reduction of diarrhea when compared to wild-type parental virus. Further, a ca mutant vaccine strain induces levels of protective antibodies in the blood samples taken from the animals after infection, which antibodies correlate with protection conferred by the vaccine. Subsequent blood samples confirm long term immunity conferred by the attenuated vaccine strain.

EXAMPLE IV

Elicitation of Protective Immunity in Clinical Trials

The attenuated virus of the invention is administered to human subjects according to well established human rotavirus vaccine protocols, as described in, e.g., Flores et al., *J. Clin. Microbiol.* 27:512–518 (1989) and Perez-Schael et al., *J. Clin. Microbiol.* 28:553–558 (1990), each of which is incorporated herein by reference. The clinical studies of the ca mutants include evaluation for safety, infectivity (virus shedding and serological response) and immunogenicity. The vaccine is initially tested in a population of adults, followed by older children, young children, infants without detectable rotavirus antibodies, and young infants with maternally-derived antibodies.

Briefly, adults or children are inoculated orally with the attenuated ca vaccine or placebo. Individuals who develop diarrhea, vomiting or nausea within the week prior to vaccination are excluded from the study. Close surveillance of subjects is carried out postvaccination by observations in various settings (e.g., home, hospital or clinic), including rectal temperatures, stool samples and venous blood samples (obtained 1–3 days before and about 4 weeks after immunization). Stools obtained during the week postvaccination are tested for rotavirus by confirmatory ELISA. Kapikian et al., in Lennette and Schmidt (ed.), *Diagnostic Procedures for Viral, Rickettsial. and Chlamydial Infections,* 5th ed., p. 927–995, Amer. Public Health Assoc., Washington, D.C. (1979). In addition, stool samples obtained postvaccination at about 3 and 5 days are titered in MA104 cells for quantity of virus present. Sera are analyzed for antibody responses by the plaque neutralization assay described above. An immunoglobulin A ELISA is also used to detect serological responses, as described in Losonsky et al., Pediatr. Infect. Dis. J. 7: 388–393 (1988). Shedding of vaccine virus is analyzed by passaging 10% suspensions of stools obtained on days 3 and 5 postvaccination into MA104 roller tube cultures. A 100 μl sample of stool specimen is pretreated with trypsin (10 μg/ml) for 1 h and inoculated onto cells maintained with modified Eagle's medium. Viral growth is monitored by cytopathic effect and/or ELISA of the culture fluid.

The attenuated virus of the vaccine is present in the stool samples of the immunized volunteers at levels approximately 500- to 1000-fold or more lower than typically found with wild-type rotavirus, and illness is not significantly associated with vaccine virus infection. Most stools obtained during the week postvaccination are negative when tested directly for rotavirus by ELISA. Further, vaccinees have a measurable rise in neutralizing antibodies to the protective rotavirus antigens of VP4 and/or VP7. Subsequent immunizations are administered periodically to the individuals as necessary to maintain sufficient levels of protective immunity.

In clinical trials conducted in adults, the cold-adapted vaccine 30° C. mutant strain D (VP4, 1A; VP7 1, also referred to as G1;P1A) (Table 2), which has a titer of $1.35 \times 10^6$ Pfu/ml, was evaluated following oral administration to 26 adult volunteers in two separate studies (eight in the initial and 25 in a later study). This 30° cold adapted, temperature sensitive strain was selected for initial clinical evaluation because it exhibited a level of temperature sensitivity that should restrict virus replication (and hence achieve attenuation) but not be too restricted so as to allow infection to induce protective immunity. The 30° C. ca D strain was tested undiluted, or at a 1:10 dilution or a 1:100 dilution, and compared to a placebo preparation. Statistically significant differences between the vaccine and placebo groups on the occurrences of gastroenteric signs or symptoms were not observed. In the second study (when rotavirus infection was not observed in the placebo group), one of seven individuals who received the undiluted vaccine developed an IgA serologic response to rotavirus antigen by ELISA. In a prior study, the same strain of rotavirus ("D") which, however, had not been passaged in tissue culture and was not cold-adapted, induced a diarrheic illness in 4 of 18 volunteers following oral administration. Thus, it appears from these studies that the 30° C. cold-adapted vaccine is safe and attenuated and is capable of multiplication in humans as demonstrated by the induction of a seroresponse to rotavirus.

The limited ability of the vaccine to multiply in immunized adults, and the absence of disease, indicates that the cold-adapted vaccine was safe, attenuated, and capable of inducing a virus specific serologic (IgA) response. As adults are typically immune to most rotavirus strains as a consequence of previous infections by wild-type virus, these results indicate that the cold-adapted vaccine strain is infectious and immunogenic.

All publications and patents mentioned in this specification are herein incorporated by reference into the specification to the same extent as if each individual publication or patent was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

TABLE 1

Selection of Cold-Adapted (ca) Mutants of Human Rotavirus (HRV) by Serial Biweekly Passage at 30° C.

| HRV Strain | Titer ($\log_{10}$ pfu/ml) of inoculum used to initiate passage series | | Titer ($\log_{10}$ pfu/ml) at Indicated Passage Level as Assayed at 30° C. | | | | | | | | | |
|---|---|---|---|---|---|---|---|---|---|---|---|---|
| | Assayed at 30° C. | Assayed at 37° C. | 1 | 2 | 3 | 4 | 5 | 6 | 7 | 8 | 9 | 10 |
| D | <1.0 | 5.0 | <1.0 | <1.0 | 2.8 | 4.2 | 4.6 | 4.6 | ND* | 4.7 | 5.3 | 5.3 |
| DS-1 | <1.0 | 6.8 | <1.0 | <1.0 | 2.8 | 2.9 | 4.2 | 4.7 | ND | 5.3 | ND | 5.0 |
| Wa × DS-1 | <1.0 | 5.4 | <1.0 | <1.0 | 2.7 | 2.8 | 4.4 | 4.8 | ND | 5.4 | ND | ND |
| Wa × P | 2.2 | 6.2 | 2.9 | 2.7 | 2.9 | 4.1 | 4.1 | 4.5 | ND | 5.3 | ND | ND |

*ND = Not Done

Procedure: ≈ $10^{5.0}$ to $10^{6.8}$ pfu of wild-type parental virus was inoculated into AGMK roller tube cultures (containing ≈ $10^6$ cells) which were incubated for one hour at 30° C. after which medium was decanted. Cultures were washed once with 1.5 ml of L-15 medium and refed with 1.5 ml of Eagle's MEM with trypsin, 0.5 μg/ml. Cultures were incubated at 30° C. for 14 days in a water bath maintained at this temperature (±0.1° C.). Cultures were then frozen and thawed and the lysate was used as inoculum (0.3 ml) to initiate the next passage at 30° C. This procedure was repeated for each of the subsequent eight passages at 30° C. Lysates from the first six passages, as well as selected passages thereafter, were titrated by plaque assay in a single test in which MA104 cell monolayers were incubated at 30° C. for 8 days.

TABLE 2

Cold-adapted Mutants of HRV: Efficiency of Plaque Formation (EOP) at Various Temperatures

| HRV Strain | Temperature of which HRV propagated* | Plaque titer at indicated temperature ($\log_{10}$ pfu/ml) | | | | | | | ca phenotype | ts phenotype |
|---|---|---|---|---|---|---|---|---|---|---|
| | | 26° C. | 28° C. | 30° C. | 36° C. | 37° C. | 38° C. | 39° | | |
| D | 37° (wt) | <1 | <1 | <1 | 5.1 | 5.0 | 5.2 | 5.1 | n/a | n/a |
| | 30° | 1.2 | 2.2 | 6.0 | 6.3 | 6.0 | <1 | <1 | 30° | 38° |
| | 28° | 5.8 | 5.7 | 6.1 | <1 | <1 | <1 | <1 | <26° | 36° |
| | 26° | 5.2 | 5.3 | 5.4 | <1 | <1 | <1 | <1 | <26° | 36° |
| DS-1 | 37° (wt) | <1 | <1 | <1 | 6.9 | 6.8 | 6.9 | 6.8 | n/a | n/a |
| | 30° | 1.6 | 4.2 | 6.8 | 6.9 | 6.7 | 5.5 | <1 | 30° | 39° |
| | 28° | 3.9 | 5.5 | 5.5 | 5.6 | 2.2 | <1 | <1 | 26° | 37° |
| | 26° | 6.1 | 6.0 | 6.2 | 5.8 | 1.2 | <1 | <1 | <26° | 37° |
| Wa × DS-1 | 37° (wt) | <1 | <1 | <1 | 5.2 | 5.4 | 5.0 | 5.1 | n/a | n/a |
| | 30° | <1 | 3.1 | 5.5 | 5.5 | 5.6 | 4.4 | <1 | 30° | 39° |
| | 28° | 3.4 | 5.9 | 6.3 | 6.0 | 1.3 | <1 | <1 | 28° | 37° |
| | 26° | 4.6 | 4.4 | 4.1 | 4.3 | 1.2 | <1 | <1 | <26° | 37° |
| Wa × P | 37° (wt) | <1 | <1 | 2.2 | 6.2 | 6.2 | 6.3 | 6.4 | n/a | n/a |
| | 30° | <1 | 4.0 | 5.7 | 6.3 | 6.4 | 3.2 | <1 | 30° | 38° |
| | 28° | 4.2 | 6.1 | 6.0 | 6.3 | 6.0 | <1 | <1 | 28° | 38° |
| | 26° | 4.9 | 5.2 | 5.0 | 5.1 | 1.2 | <1 | <1 | <26° | 37° | n/a = not applicable
wt = wild-type
ts = Highest temperature at which plaque titer is reduced $10^2$ or more compared to highest titer attained.
ca = Lowest temperature at which plaque titer is reduced less than $10^2$ compared to highest titer attained.
*HRV propagated at indicated temperature for 10 passages after which a clonal population was derived by three successive plaque to plaque passages. Uncloned virus was used to initiate the next serial passage series at a lower temperature. Efficiency of plaque formation assays performed using triply plaque purified virus.

What is claimed is:

1. A human rotavirus composition which comprises a cloned, genetically stable, live, cold adapted, temperature sensitive, attenuated human rotavirus of serogroup A wherein the attenuated rotavirus displays increased replication efficiency as compared to wild-type rotavirus when cultured in vitro at a temperature between 26 to 30° C. and the attenuated rotavirus displays a decreased replication efficiency as compared to wild-type rotavirus when cultured in vitro at a temperature between 36 to 39° C., while retaining the ability to induce an immune response in a human host without causing a severe lower gastrointestinal infection.

2. The human rotavirus composition of claim 1, further comprising a physiologically acceptable carrier.

3. The human rotavirus composition of claim 1, which further comprises an adjuvant to enhance the immune response.

4. The human rotavirus composition of claim 1, wherein the attenuated rotavirus is a genetic reassortant of at least two strains of human rotavirus.

5. The human rotavirus composition of claim 1, wherein the attenuated rotavirus is of a VP4 1A or VP4 1B serotype and VP7 1, VP7 2, VP7 3 or VP7 4 serotype.

6. The human rotavirus composition of claim 5, wherein the serotype is VP4 1A and VP7 1, VP4 1B and VP7 2, VP4 1A and VP7 3, or VP4 1A and VP7 4.

7. The human rotavirus composition of claim 5, wherein the attenuated rotavirus is serotype VP4 1 A, VP7 1.

8. The human rotavirus composition of claim 7, wherein the attenuated rotavirus serotype VP4 1A, VP7 1 is derived from human rotavirus strain D.

9. The human rotavirus composition of claim 8, wherein the attenuated rotavirus strain D is not restricted in its ability to produce plaques in African Green Monkey kidney (AGMK) cells at 30° C.

10. The human rotavirus composition of claim 5, wherein the composition comprises four attenuated human rotaviruses, one from each of serotype VP7 1, VP7 2, VP7 3, and VP7 4.

11. The human rotavirus composition of claim 1, wherein the rotavirus is not restricted in its ability to produce plaques in AGMK cells at 30° C.

12. The human rotavirus composition of claim 11, wherein the rotavirus is not restricted in its ability to produce plaques in AGMK cells at 28° C.

13. The human rotavirus composition of claim 11, wherein the rotavirus is not restricted in its ability to produce plaques in AGMK cells at 26° C.

14. The human rotavirus composition of claim 1, wherein the cold-adapted human rotavirus contains mutations that render the virus temperature-sensitive.

15. The human rotavirus composition of claim 14, wherein the rotavirus is restricted in its ability to replicate at 39° C.

16. The human rotavirus composition of claim 15, wherein the rotavirus is restricted in its ability to replicate at 38° C.

17. The human rotavirus composition of claim 16, wherein the rotavirus is restricted in its ability to replicate at 37° C.

18. The human rotavirus composition of claim 17, wherein the rotavirus is restricted in its ability to replicate at 36° C.

19. The composition of claim 1, formulated in a dose of $10^3$ to about $10^6$ PFU of attenuated rotavirus.

20. The human rotavirus composition of claim 2, wherein the physiologically acceptable carrier is a citrate buffer.

21. The human rotavirus composition of claim 1 which is lyophilized.

22. A method for stimulating the immune system of an individual to induce an immune response against human rotavirus without causing a severe lower gastrointestinal infection, which comprises:

administering to the individual an immunologically sufficient amount of a composition which comprises a cloned, genetically stable, live, cold adapted, temperature sensitive, attenuated human rotavirus of serogroup A wherein the attenuated rotavirus displays increased replication efficiency as compared to wild-type rotavirus when cultured in vitro at a temperature between 26 to 30° C. and the attenuated rotavirus displays a decreased replication efficiency as compared to wild-type rotavirus when cultured in vitro at a temperature between 36 to 39° C., while retaining the ability to induce an immune response in a human host in a physiologically acceptable carrier.

23. The method of claim 22, wherein the composition further comprises an adjuvant to enhance the immune response.

24. The method of claim 22, wherein the attenuated rotavirus is a genetic reassortant of at least two strains of human rotavirus.

25. The method of claim 22, wherein the attenuated rotavirus is of a VP4 1A or VP4 1B serotype and VP7 1, VP7 2, or VP7 3 or VP7 4 serotype.

26. The method of claim 25, wherein the attenuated human rotavirus serotype is VP41 A and VP7 1, VP4 1B and VP7 2, VP4 1A and VP7 3 or VP4 1A and VP7 4.

27. The method of claim 25, wherein the attenuated rotavirus is serotype VP4 1A, VP7 1.

28. The method of claim 27, wherein the attenuated rotavirus serotype VP4 1A, VP7 1 is derived from human rotavirus strain D.

29. The method of claim 28, wherein the attenuated rotavirus strain D is not restricted in its ability to produce plaques in AGMK cells at 30° C.

30. The method of claim 22, wherein the human rotavirus is not restricted in its ability to produce plaques in AGMK cells at 30° C.

31. The method of claim 30, wherein the human rotavirus is not restricted in its ability to produce plaques in AGMK cells at 28° C. or 26° C.

32. The method of claim 22, wherein the human rotavirus is restricted in its ability to replicate at 39° C.

33. The method of claim 32, wherein the human rotavirus is restricted in its ability to replicate at 38° C.

34. The method of claim 33, wherein the human rotavirus is restricted in its ability to replicate at 37° C.

35. The method of claim 22, wherein the attenuated human rotavirus is administered to the individual in a amount of $10^3$ to about $10^6$ PFU.

36. The method of claim 22, wherein the attenuated human rotavirus is administered to the alimentary tract of said individual.

37. The method of claim 36, wherein the attenuated virus is administered in a liquid suspension.

38. The method of claim 22, wherein the attenuated virus is administered to an individual seronegative for antibodies to said virus.

39. The method of claim 22, wherein the administration of attenuated virus to said individual is repeated at least one month after an initial administration.

40. A human rotavirus composition which comprises a cloned, genetically stable, live, cold adapted, temperature sensitive, attenuated human rotavirus of serogroup A selected at 30° C., wherein said human rotavirus is not restricted in its ability to produce plaques in AGMK cells at 30° C. and is restricted in its ability to produce plaques in AGMK cells at 38° C. or at 39° C.

41. The cloned stable human rotavirus of claim 40, wherein the rotavirus is serotype VP4 1A and VP7 1, VP4 1B and VP7 2 or is a cloned stable reassortant rotavirus having serotype VP4 1a and VP7 2, or VP4 1a and VP7 3.

42. A human rotavirus composition which comprises a cloned, genetically stable, live, cold adapted, temperature sensitive, attenuated human rotavirus of serotype A selected at 26° C. or 28° C., wherein said human rotavirus is not restricted in its ability to produce plaques in AGMK cells at less than 26° C. and is restricted in its ability to produce plaques in AGMK cells at 36° C.

43. The cloned stable human rotavirus of claim 42, wherein the rotavirus is serotype VP4 1A and VP7 1.

44. A human rotavirus composition which comprises a cloned, genetically stable, live, cold adapted, temperature sensitive, attenuated human rotavirus of serogroup A selected at 28° C., wherein said human rotavirus is not restricted in its ability to produce plaques in AGMK cells at 26° C. or 28° C. and is restricted in its ability to produce plaques in AGMK cells at 37° C.

45. The cloned stable human rotavirus of claim 44, wherein the rotavirus is serotype VP4 1b and VP7 2 or is a reassortant rotavirus having serotype VP4 1a and VP7 2.

46. A human rotavirus composition which comprises a cloned, genetically stable, live, cold adapted, temperature sensitive, attenuated human rotavirus of serogroup A selected at 28° C., wherein said human rotavirus is not restricted in its ability to produce plaques in AGMK cells at 26° C. and is restricted in its ability to produce plaques in AGMK cells at 37° C.

47. The cloned stable human rotavirus of claim 46, wherein said rotavirus is serotype VP4 1b and VP7 2.

48. A human rotavirus composition which comprises a cloned, genetically stable, live, cold adapted, temperature sensitive, attenuated human rotavirus of serogroup A selected at 26° C., wherein said human rotavirus is not restricted in its ability to produce plaques in AGMK cells at less than 26° C. and is restricted in its ability to produce plaques in AGMK cells at 37° C.

49. The cloned stable human rotavirus of claim 48, wherein said rotavirus is serotype VP4 1b and VP7 2, or a reassortant rotavirus having serotype VP4 1a and VP7 2, or VP4 1a and VP7 3.

* * * * *